United States Patent [19]

Fuchs et al.

[11] Patent Number: 5,502,070
[45] Date of Patent: Mar. 26, 1996

[54] SUBSTITUTED 3,4-HETARYL-PYRAZOLINES

[75] Inventors: Rainer Fuchs, Wuppertal; Reiner Fischer, Monheim; Christoph Erdelen, Leichlingen; Wilhelm Stendel, Wuppertal, all of Germany

[73] Assignee: Bayer Aktiengesellschaft, Leverkusen, Germany

[21] Appl. No.: 129,923

[22] Filed: Sep. 30, 1993

[30] Foreign Application Priority Data

Oct. 7, 1992 [DE] Germany .......................... 42 33 717.8

[51] Int. Cl.⁶ ...................... C07D 403/14; A01N 47/38
[52] U.S. Cl. .................... 514/406; 546/256; 548/365.4
[58] Field of Search ..................... 546/256; 548/365.4; 514/406

[56] References Cited

U.S. PATENT DOCUMENTS

| | | |
|---|---|---|
| 4,070,365 | 1/1978 | van Daalen et al. . |
| 4,174,393 | 11/1979 | van Daalen et al. . |
| 5,068,241 | 11/1991 | Fuchs et al. . |
| 5,247,094 | 9/1993 | Fuchs ................................. 548/268.4 |
| 5,250,532 | 10/1993 | McLaren ............................. 514/256 |

FOREIGN PATENT DOCUMENTS

| | | |
|---|---|---|
| 466408 | 7/1991 | European Pat. Off. . |
| 0466408 | 1/1992 | European Pat. Off. . |
| 0508469 | 10/1992 | European Pat. Off. . |
| 1514285 | 6/1978 | United Kingdom . |
| 9429300 | 12/1994 | WIPO . |

OTHER PUBLICATIONS

McOmie, Protective Groups in Organic Chemistry pp. 53–61 (1975).
Chemical Abstract, p. 811, 28–Heterocycles, vol. 118, 1993.

*Primary Examiner*—Robert Gerstl
*Attorney, Agent, or Firm*—Sprung Horn Kramer & Wood

[57] ABSTRACT

The present invention relates to new substituted 3,4-hetaryl-pyrazolines of the general formula (I)

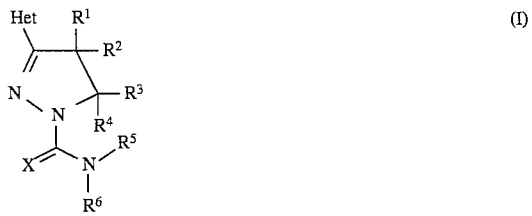

in which $R^1$ represents an unsaturated five- or six-membered optionally substituted and optionally benzo-fused heterocyclic ring containing 1 to 4 nitrogen atoms, or represents an optionally substituted heterocyclic ring from the series comprising

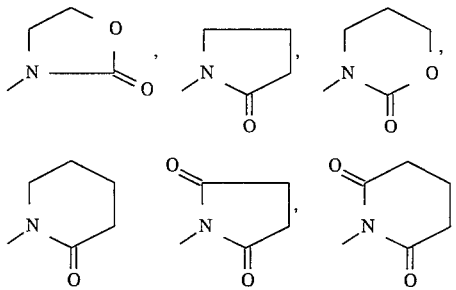

X represents oxygen or sulphur and Het represents an optionally substituted and/or optionally fused heterocyclic ring, processes for their preparation and their use as agents for combating pests.

6 Claims, No Drawings

SUBSTITUTED 3,4-HETARYL-PYRAZOLINES

The invention relates to new substituted 3,4-hetaryl-pyrazolines, several processes for their preparation and their use as agents for combating pests.

It is known that certain substituted pyrazoline derivatives have a good activity against animal pests.

In this context, see, for example, DE-A 2 700 258, U.S. Pat. No. 4,174,393, DE-A 2 529 689, U.S. Pat. No. 4,070,365 and EP 0 466 408, DE-A 4 001 931, DE-A 4 117 076, U.S. Pat. No. 5,068,241.

However, the level of action or duration of action of these already known compounds is not completely satisfactory in all fields of use, especially against certain organisms or when low concentrations are used.

New substituted 3,4-hetaryl-pyrazolines of the general formula (I)

[Structure of formula (I)]

in which $R^1$ represents an unsaturated five- or six-membered optionally substituted and optionally benzo-fused heterocyclic ring containing 1 to 4 nitrogen atoms, or represents an optionally substituted heterocyclic ring from the series comprising

[Structures of heterocyclic rings]

$R^2$ represents hydrogen, alkyl, optionally substituted cycloalkyl, halogenoalkyl, halogenoalkylthio or alkoxycarbonyl, $R^3$ represents hydrogen or alkyl, $R^4$ represents hydrogen or alkyl, $R^5$ represents hydrogen, alkyl, phenyl or alkylthio, $R^6$ represents optionally substituted alkyl, optionally substituted cycloalkyl or the radical

[Structure with $R^{10}$ and $R^{11}$]

wherein $R^{10}$ and $R^{11}$ can be identical or different and represent hydrogen, halogen, alkyl, nitro, cyano, halogenoalkyl, alkoxy, halogenoalkoxy, alkylthio, halogenoalkylthio, optionally substituted phenoxy, optionally substituted mono- or dialkylamino, optionally substituted cycloalkyl, alkoxycarbonyl, optionally substituted arylthio, alkenyloxy, alkinyl, alkylthionyl, alkylsulphonyl, halogenoalkylthionyl, halogenoalkylsulphonyl or halogenoalkoxycarbonyl, or wherein $R^{10}$ and $R^{11}$ together represent a divalent optionally substituted radical which optionally contains one or two oxygen atoms, X represents oxygen or sulphur and Het represents an optionally substituted and/or optionally fused heterocyclic ring, have been found.

It has furthermore been found that the new substituted 3,4-hetaryl-pyrazolines of the general formula I in which

[Structure of formula (I)]

$R^1$ represents an unsaturated five- or six-membered optionally substituted and optionally benzo-fused heterocyclic ring containing 1 to 4 nitrogen atoms, or represents an optionally substituted heterocyclic ring from the series comprising

[Structures of heterocyclic rings]

$R^2$ represents hydrogen, alkyl, optionally substituted cycloalkyl, halogenoalkyl, halogenoalkylthio or alkoxycarbonyl, $R^3$ represents hydrogen or alkyl, $R^4$ represents hydrogen or alkyl, $R^5$ represents hydrogen, alkyl, phenyl or alkylthio, $R^6$ represents optionally substituted alkyl, optionally substituted cycloalkyl or the radical

[Structure with $R^{10}$ and $R^{11}$]

wherein $R^{10}$ and $R^{11}$ can be identical or different and represent hydrogen, haloen, alkyl, nitro, cyano, halogenoalkyl, alkoxy, halogenoalkoxy, alkylthio, halogenoalkylthio, optionally substituted phenoxy, optionally substituted mono- or dialkylamino, optionally substituted cycloalkyl, alkoxycarbonyl, optionally substituted arylthio, alkenyloxy, alkinyl, alkylhionyl, alkylsulphonyl, halogenoalkylthionyl, halogenoalkylsulphonyl or halogenolkxycarbonyl, or wherein $R^{10}$ and $R^{11}$ together represent a divalent optionally substituted radical which optionally contains one or two oxygen atoms, X represents oxygen or sulphur and Het represents an optionally substituted and/or optionally fused heterocyclic ring, are obtained by a process in which (A) to obtain substituted 3,4-hetaryl-pyrazolines of the formula (I) in which $R^5$ represents hydrogen, pyrazoline derivatives of the formula (II)

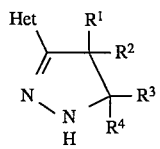  (II)

in which $R^1$, $R^2$, $R^3$, $R^4$ and Het have the abovementioned meaning, are reacted with isocyanates or isothiocyanates of the formula (III)

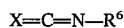  (III)

in which

X and $R^6$ have the abovementioned meaning, if appropriate in the present of bases, or by a process in which (B) pyrazoline derivatives of the formula (II)

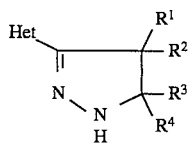  (II)

in which $R^1$, $R^2$, $R^3$, $R^4$ and Het have the abovementioned meaning, are reacted with compounds of the formula (IV)

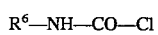  (IV)

in which $R^6$ has the abovementioned meaning, if appropriate in the presence of a solvent and if appropriate in the presence of bases.

Finally, it has been found that the new substituted 3,4-hetaryl-pyrazolines of the general formula (I) have a very good action against pests, and in particular a very good insecticidal and acaricidal activity.

Surprisingly, the substituted 3,4-hetaryl-pyrazolines according to the invention display a considerably better insecticidal activity against insects and arachnids which are phytopathogenic and parasitise warm-blooded animals than compounds which are known from the prior art and are close chemically and in terms of their action.

Formula (I) provides a general definition of the substituted 3,4-hetaryl-pyrazolines according to the invention. Preferred compounds of the formula (I) are those in which $R^1$ represents an optionally substituted pyrrolyl, pyrazolyl, imidazolyl, 1,2,3-triazolyl, 1,2,4-triazolyl, tetrazolyl, pyridinyl, pyridonyl, pyrimidinyl, pyrimidonyl, pyrazinyl, pyridazinyl or triazinyl radical, which furthermore represents an optionally substituted azolinone, azolinethione or azolinimino radical, bonded via nitrogen, from the series comprising

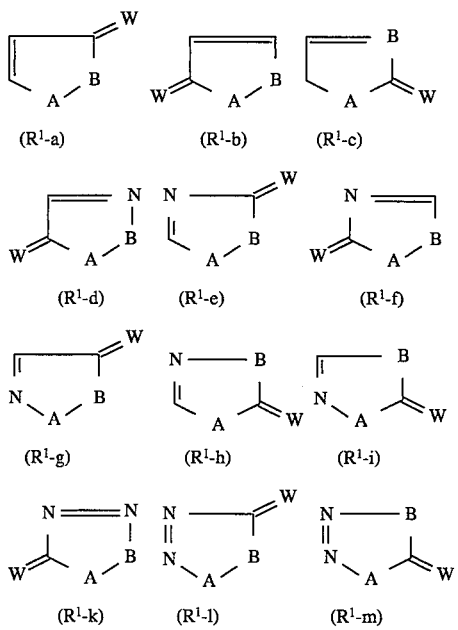

wherein one of the groups A or B represents nitrogen and in each case the other (A or B) represents oxygen or sulphur, or represents the group —N-alkyl ($C_1$–$C_4$—), or represents a methylene grouping —$CH_2$— or a —CH— group, W represents oxygen or sulphur, or represents the group —N-alkyl ($C_1$–$C_4$—), or furthermore represents an optionally substituted heterocyclic ring from the series comprising

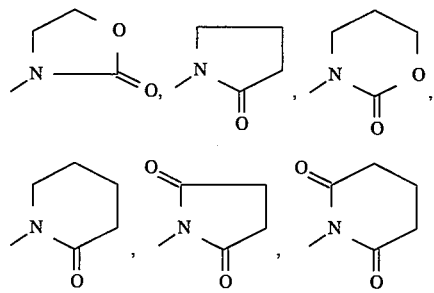

wherein the following substituents are in each case possible for the abovementioned heterocyclic rings: halogen, cyano, nitro, hydroxyl, amino, alkyl ($C_1$–$C_6$), alkoxy ($C_1$–$C_6$), alkyl($C_1$–$C_6$)thio, halogenoalkyl ($C_1$–$C_4$), halogenoalkoxy($C_1$–$C_4$), halogenoalkyl($C_1$–$C_4$)thio, alkyl($C_1$–$C_6$)amino, dialkyl($C_1$–$C_6$)amino, dihalogenoalkyl($C_1$–$C_4$)amino, alkoxy($C_1$–$C_6$)carbonyl and phenyl which is optionally substituted by halogen, alkyl($C_1$–$C_4$), alkoxy($C_1$–$C_4$), halogenoalkyl($C_1$–$C_4$), halogenoalkoxy ($C_1$–$C_6$) or halogenalkyl($C_1$–$C_4$)thio, $R^2$ represents hydrogen, alkyl($C_1$–$C_6$), cycloalkyl($C_3$–$C_7$) which is optionally substituted by halogen or halogenaolkyl($C_1$–$C_4$); halogenoalkyl($C_1$–$C_4$)thio or alkoxy($C_1$–$C_6$)carbonyl, $R^3$ represents hydrogen or alkyl($C_1$–$C_6$), $R^4$ represents hydrogen or alkyl($C_1$–$C_6$), $R^5$ represents hydrogen, alkyl($C_1$–$C_6$), phenyl or alkyl($C_1$–$C_4$)thio, $R^6$ represents alkyl($C_1$–$C_6$) which is optionally substituted by halogen, halogenoalkyl($C_1$–$C_4$) or halogenoalkoxy ($C_1$–$C_4$), or represents cycloalkyl($C_3$–$C_7$) which is optionally substituted by halogen, halogenoalkyl($C_1$–$C_4$) or halogenoalkoxy($C_1$–$C_4$), or represents the radical

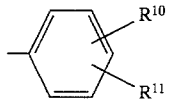

wherein $R^{10}$ and $R^{11}$ can be identical or different and represent hydrogen, halogen, alkyl($C_1$–$C_6$), nitro, cyano, halogenoalkyl($C_1$–$C_4$), alkoxy($C_1$–$C_6$), halogenoalkoxy ($C_1$–$C_4$), alkyl($C_1$–$C_4$)thio, halogenoalkyl($C_1$–$C_4$)thio, phenoxy or phenylthio which is optionally substituted by halogen, halogenoalkyl($C_1$–$C_4$), alkoxy($C_1$–$C_4$) or alkyl($C_1$–$C_4$), mono- or dialkylamino having in each case 1 to 6 carbon atoms in the alkyl radical and optionally substituted by halogen, alkoxy($C_1$–$C_4$) or halogenoalkyl($C_1$–$C_4$), cycloalkyl($C_3$–$C_7$) which is optionally substituted by alkyl($C_1$–$C_4$), alkoxy($C_1$–$C_4$), halogen or alkyl($C_1$–$C_4$)thio, alkoxy($C_1C_4$)carbonyl, alkenyl ($C_2$–$C_6$)oxy, alkinyl ($C_2$–$C_6$), alkyl($C_1$–$C_4$)thionyl, alkyl($C_1$–$C_4$)sulphonyl, halogenoalkyl($C_1$–$C_4$)thionyl, halogenoalkyl($C_1$–$C_4$)sulphonyl or halogenoalkoxy($C_1$–$C_4$)-carbonyl, or wherein $R^{10}$ and $R^{11}$ together represent one of the following divalent radicals

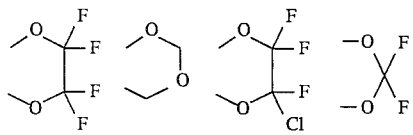

X represents oxygen or sulphur and

Het represents an optionally benzo-fused heteroaromatic 5- or 6-membered ring which is unsubstituted or mono- to polysubstituted by identical or different substituents and contains identical or different, one or more hetero atoms, such as oxygen, sulphur and nitrogen, possible substituents being alkyl, halogen, halogenoalkyl, alkoxy, alkylthio, halogenoalkoxy, halogenoalkylthio, alkoxycarbonyl, halogenoalkoxycarbonyl, optionally substituted aryloxy, optionally substituted arylthio, alkenyloxy, alkinyl, alkylthionyl, alkylsulphonyl, halogenoalkylthionyl, halogenoalkylsulphonyl, nitro or cyano, or wherein two adjacent positions are bonded to one another by a 3,4-methylenedioxyl or 3,4-ethylenedioxyl radical which is substituted by halogen.

Particularly preferred compounds of the formula (I) are those in which $R^1$ represents an optionally substituted pyrrolyl, pyrazolyl, imidazolyl, 1,2,3-triazolyl, tetrazolyl, pyridinyl, pyridonyl, pyrimidinyl, pyrimidonyl, pyrazinyl, pyridazinyl, 1,2,4-triazolyl or triazinyl radical, or $R^1$ furthermore represents an azolinone, azolinethione or azolinimino radical, which is substituted or mono- or disubstituted by identical or different substituents and bonded via nitrogen, from the series comprising

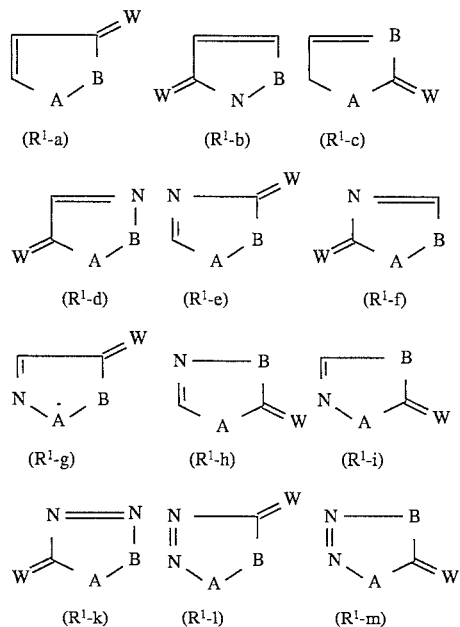

wherein one of the groups A or B represents nitrogen and in each case the other (A or B) represents oxygen or sulphur, or represents the group —N-alkyl($C_1$–$C_4$—), or represents a methylene grouping —$CH_2$— or a CH group, W represents oxygen or sulphur, or represents the group —N-alkyl($C_1$–$C_4$—), or $R^1$ furthermore represents a heterocyclic ring, which is unsubstituted or mono- to trisubstituted, from the series comprising

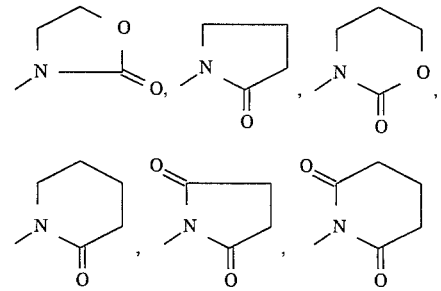

wherein the following substituents are in each case possible for the abovementioned heterocyclic rings: fluorine, chlorine, bromine, iodine, cyano, nitro, hydroxyl, amino, alkyl($C_1$–$C_4$), alkoxy($C_1$–$C_4$), alkyl($C_1$–$C_4$)thio, halogenoalkyl($C_1$–$C_2$), halogenoalkoxy($C_1$–$C_2$), halogenoalkyl($C_1$–$C_2$)thio, alkyl($C_1$–$C_3$)amino, dialkyl($C_1$–$C_3$)amino, dihalogenoalkyl($C_1$–$C_2$)amino, alkoxy($C_1$–$C_4$)carbonyl and phenyl which is optionally substituted by fluorine, chlorine, bromine, methyl, ethyl, methoxy, ethoxy, halogenoalkyl($C_1$–$C_2$), halogenoalkoxy ($C_1$–$C_2$) or halogenoalkyl($C_1$–$C_2$)thio, $R^2$ represents hydrogen, alkyl($C_1$–$C_4$), cycloalkyl($C_3$–$C_6$) which is optionally substituted by fluorine, chlorine, bromine or halogenoalkyl($C_1$–$C_3$); halogenoalkyl($C_1$–$C_3$)thio or alkoxy($C_1$–$C_4$)carbonyl, $R^3$ represents hydrogen or alkyl($C_1$–$C_4$), $R^4$ represents hydrogen or alkyl($C_1$–$C_4$), $R^5$ represents hydrogen, alkyl($C_1$–$C_4$), phenyl or alkyl($C_1$–$C_3$)thio, $R^6$ represents alkyl($C_1$–$C_4$) which is optionally substituted by fluorine, chlorine, bromine, halogenoalkyl($C_1$–$C_3$) or halogenoalkoxy($C_1$–$C_3$), or represents cycloalkyl($C_3$–$C_6$) which is optionally substituted by fluorine, chlorine, bromine, halogenoalkyl($C_1$–$C_3$) or halogenoalkoxy($C_1$–$C_3$), or represents the radical

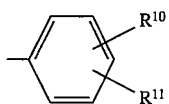

wherein $R^{10}$ and $R^{11}$ can be identical or different and represent hydrogen, fluorine, chlorine, bromine, iodine, alkyl($C_1$–$C_4$), nitro, cyano, halogenoalkyl($C_1$–$C_3$), alkoxy($C_1$–$C_4$), halogenoalkoxy($C_1$–$C_3$), alkyl($C_1$–$C_3$)thio, halogenoalkyl($C_1$–$C_3$)thio, phenoxy which is optionally substituted by fluorine, chlorine, bromine, halogenoalkyl($C_1$–$C_3$), alkoxy($C_1$–$C_3$) or alkyl($C_1$–$C_3$), mono- or dialkylamino having in each case 1 to 4 carbon atoms in the alkyl radical and optionally substituted by fluorine, chlorine, bromine, alkoxy($C_1$–$C_3$) or halogenoalkyl($C_1$–$C_3$), or cycloalkyl($C_3$–$C_6$) which is optionally substituted by alkyl($C_1$–$C_3$), alkoxy($C_1$–$C_3$), fluorine, chlorine, bromine or alkyl($C_1$–$C_3$)thio, or wherein $R^{10}$ and $R^{11}$ together represent one of the following divalent radicals

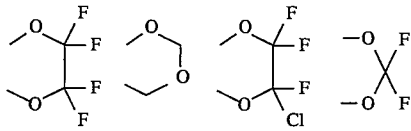

X represents oxygen or sulphur and

Het represents a heteroaromatic 5- or 6-membered ring which is unsubstituted or mono- to trisubstituted by identical or different substituents and contains identical or different, one or more hetero atoms, such as oxygen, sulphur or nitrogen, substituents which may be mentioned being: alkyl($C_1$–$C_4$), fluorine, chlorine, bromine, halogenoalkyl($C_1$–$C_4$), alkoxy($C_1$–$C_4$), alkyl($C_1$–$C_4$)thio, halogenoalkoxy($C_1$–$C_3$), halogenoalkyl($C_1$–$C_3$)thio, alkoxy($C_1$–$C_3$)carbonyl, phenoxy or phenylthio which is optionally substituted by fluorine, chlorine, bromine, alkyl($C_1$–$C_3$), alkoxy($C_1$–$C_3$) or halogenoalkoxy($C_1$–$C_3$), alkenyl($C_2$–$C_4$)oxy, alkinyl($C_2$–$C_4$), alkyl($C_1$–$C_3$)thionyl, alkyl($C_1$–$C_3$)sulphonyl, halogenoalkyl($C_1$–$C_3$)thionyl, halogenoalkyl($C_1$–$C_3$)sulphonyl, nitro or cyano, or wherein two adjacent positions are bonded to one another by a 3,4-methylenedioxy or 3,4-ethylenedioxy radical which is substituted by fluorine and/or chlorine.

Especially preferred compounds of the formula (I) are those in which $R^1$ an optionally substituted pyrrolyl, pyrazolyl, imidazolyl, 1,2,3-triazolyl, 1,2,4-triazolyl, tetrazolyl, pyridinyl, pyridonyl, pyrimidinyl, pyrimidonyl, pyrazinyl, pyridazinyl or triazinyl radical, or $R^1$ furthermore represents an azolinone, azolinethione or azoliniminine radical, which is unsubstituted or mono- or disubstituted by identical or different substituents and bonded via nitrogen, from the series comprising

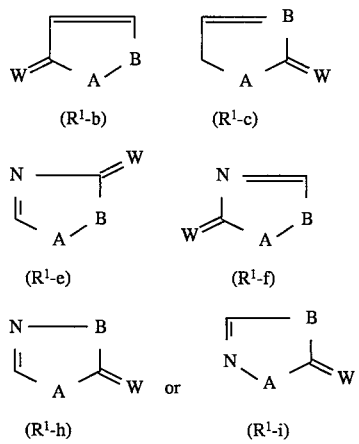

wherein one of the groups A or B represents nitrogen and in each case the other (A or B) represents oxygen or sulphur, or represents the group —N-alkyl($C_1$–$C_4$—), or represents a methylene grouping —$CH_2$— or a —CH— group, W represents oxygen or sulphur, or $R^1$ furthermore represents a heterocyclic ring which is unsubstituted or mono- to trisubstituted, from the series comprising

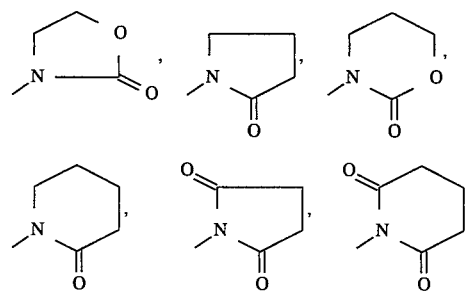

in each case the following substituents being possible for the abovementioned heterocyclic rings: fluorine, chlorine, bromine, iodine, cyano, nitro, hydroxyl, amino, methyl, ethyl, n-propyl, i-propyl, t-butyl, methoxy, ethoxy, methylthio, ethylthio, halogenoalkyl($C_1$–$C_2$), halogenoalkoxy($C_1$–$C_2$) or halo- genoalkyl($C_1$–$C_2$)thio having in each case 1 to 5 fluorine and/or chlorine atoms, methylamino, dimethylamino, methoxycarbonyl and phenyl which is optionally substituted by fluorine, chlorine, bromine, methyl, ethyl, methoxy, ethoxy or halogenoalkoxy($C_1$–$C_2$) or halogenoalkyl($C_1$–$C_2$)thio having in each case 1 to 5 fluorine and/or chlorine atoms, $R^2$ represents hydrogen, methyl, ethyl, n-propyl, i-propyl or alkoxy($C_1$–$C_2$)carbonyl, $R^3$ represents hydrogen, methyl, ethyl, n-propyl or i-propyl, $R^4$ represents hydrogen, methyl, ethyl or n-propyl, $R^5$ represents hydrogen, methyl, ethyl, n-propyl, i-propyl, phenyl or alkyl($C_1$–$C_2$)thio, $R^6$ represents methyl, ethyl, n-propyl or i-propyl which are optionally substituted by fluorine, chlorine, halogenoalkyl($C_1$–$C_3$) or halogenoalkoxy($C_1$–$C_3$), or represents cycloalkyl($C_3$–$C_6$) which is optionally substituted by fluorine, chlorine, halogenoalkyl($C_1$–$C_3$) or halogenoalkoxy($C_1$–$C_3$), or represents the radical

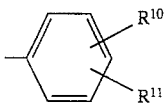

wherein
$R^{10}$ and $R^{11}$ can be identical or different and represent hydrogen, fluorine, chlorine, bromine, iodine, methyl, ethyl, n-propyl, i-propyl, tertbutyl, nitro, cyano, halogenoalkyl($C_1$–$C_3$), alkoxy($C_1$–$C_3$), halogenoalkoxy($C_1$–$C_3$), alkyl($C_1$–$C_3$)thio, halogenoalkyl($C_1$–$C_3$)thio, phenoxy which is optionally substituted by fluorine, chlorine, halogenoalkyl($C_1$–$C_3$), methoxy, ethoxy, methyl or ethyl, mono- or dialkylamino having in each case 1 to 3 carbon atoms in the alkyl radical and optionally substituted by fluorine, chlorine, methoxy, ethoxy or halogenoalkyl($C_1$–$C_3$), or cycloalkyl($C_{1'-C6}$) which is optionally substituted by methyl, ethyl, methoxy, ethoxy, fluorine, chlorine or alkyl($C_1$–$C_3$)thio, or wherein
$R^{10}$ and $R^{11}$ together represent one of the following divalent radicals

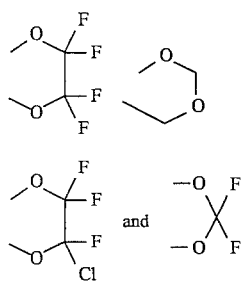

X represents oxygen or sulphur and
Het represents a pyridyl, pyrazinyl, thiazolyl, pyrimidyl, pyridazinyl, thienyl, furyl, oxazolyl or pyrrolyl radical which is in each case unsubstituted or mono- to trisubstituted by identical or different substituents, substituents which may be mentioned being: methyl, ethyl, n-propyl, i-propyl, tert-butyl, fluorine, chlorine, bromine, iodine, halogenoalkyl($C_1$–$C_3$), methoxy, ethoxy, n-propyloxy, i-propyloxy, alkyl($C_1$–$C_3$)thio, halogenoalkoxy($C_1$–$C_3$), halogenoalkyl ($C_1$–$C_3$)thio, alkoxy($C_1$–$C_3$)carbonyl, phenoxy or phenylthio which is optionally substituted by fluorine, chlorine, bromine, methyl, ethyl, methoxy, ethoxy or halogenoalkyl($C_1$–$C_3$), alkenyl ($C_3$–$C_4$)oxy, alkinyl($C_2$–$C_4$), alkyl($C_1$–$C_3$)thionyl, alkyl($C_1$–$C_3$)sulphonyl, halogenoalkyl($C_1$–$C_3$)thionyl, halogenoalkyl($C_1$–$C_3$)sulphonyl, nitro or cyano, or wherein two adjacent positions are bonded to one another by a 3,4-methylenedioxy or 3,4-ethylenedioxy radical which is substituted by fluorine and/or chlorine.

A group of exceptionally preferred compounds of the formula (I) comprises those in which
$R^1$ represents an optionally substituted pyrrolyl, pyrazolyl, imidazolyl, 1,2,3-triazolyl, 1,2,4-triazolyl, tetrazolyl, pyridinyl, pyridonyl, pyrimidinyl, pyrazinyl, pyridazinyl or triazinyl radical,
$R^1$ furthermore represents an azolinone, azolinethione or azolinimine radical, which is unsubstituted or mono- or disubstituted by identical or different substituents and bonded via nitrogen, from the series comprising

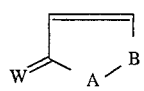 (R$^1$-b)

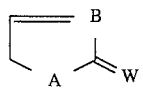 (R$^1$-c)

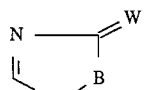 (R$^1$-e)

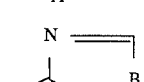 (R$^1$-f)

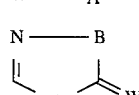 (R$^1$-h)

oder

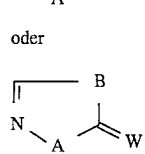 (R$^1$-i)

wherein
one of the groups A or B represents nitrogen and in each case the other (A or B) represents oxygen or sulphur, or represents the group —N-alkyl($C_1$–$C_4$—), or represents a methylene grouping —$CH_2$— or a —CH— group,
W represents oxygen or sulphur, or
in each case the following substituents being possible for the abovementioned heterocyclic rings: fluorine, chlorine, bromine, iodine, cyano, nitro, hydroxyl, amino, methyl, ethyl, n-propyl, i-propyl, t-butyl, methoxy, ethoxy, methylthio, ethylthio, halogenoalkoxy($C_1$–$C_2$), halogenoalkoxy($C_1$–$C_2$) or halogenoalkyl($C_1$–$C_2$)thio having in each case 1 to 5 fluorine and/or chlorine atoms, methylamino, dimethylamino, methoxycarbonyl and phenyl which is optionally substituted by fluorine, chlorine, bromine, methyl, ethyl, methoxy, ethoxy and halogenoalkoxy ($C_1$–$C_2$) or halogenoalkyl($C_1$–$C_2$)thio having in each case 1 to 5 fluorine and/or chlorine atoms, and
$R^2$, $R^3$, $R^4$, $R^5$, $R^6$, X and Het have the abovementioned meaning.

The substituent meaning halogenoalkyl in the radicals halogenoalkyl, halogenoalkoxy, halogenoalkylthio, halogenoalkylthionyl and halogenoalkylsulphonyl preferably contains 1 to 4, in particular 1 or 2, carbon atoms, and preferably 1 to 5, in particular 1 to 3, identical or different halogen atoms, halogen atoms being preferably fluorine, chlorine and bromine, in particular fluorine and chlorine. Examples which may be mentioned are trifluoromethyl, chlorodifluoromethyl, bromomethyl, 2,2,2-trifluoroethyl and pentafluoroethyl.

The following substituted 3,4-hetaryl-pyrazolines of the formula (I) listed in Table 1 may be mentioned specifically by way of example, but not by way of limitation, in addition to the compounds mentioned in the preparation examples:

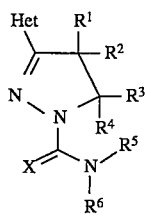

(I)

| Het | R¹ | R² | R³ | R⁴ | R⁵ | R⁶ | X |
|---|---|---|---|---|---|---|---|
| 2-pyridyl | pyrazol-1-yl | H | H | H | H | 4-Cl-phenyl | O |
| 5-Br-2-pyridyl | 5-Cl-pyrazol-1-yl | H | H | H | H | 4-Br-phenyl | O |
| 2-pyridyl | 4-Br-pyrazol-1-yl | H | H | H | H | 4-CF₃-phenyl | O |
| 3-pyridyl | 4-I-pyrazol-1-yl | H | H | H | H | 4-OCF₃-phenyl | O |
| 2-Cl-5-pyridyl | 4-CH₃-pyrazol-1-yl | H | H | H | H | 4-SCF₃-phenyl | O |
| 2-Cl-5-pyridyl | pyrazol-1-yl | H | H | H | H | 4-Cl-phenyl | O |
| 4-pyridyl | 4-Cl-pyrazol-1-yl | CH₃ | H | H | H | 4-SCH₃-phenyl | O |
| 4-pyridyl | 1,2,4-triazol-1-yl | H | H | H | H | 4-NO₂-phenyl | O |
| 2-pyrazinyl | 5-Cl-1,2,4-triazol-1-yl | CH₂C(O)OCH₃ | H | H | H | 4-OCHF₂-phenyl | O |
| 2-pyrazinyl | 4-Cl-pyrazol-1-yl | H | H | H | H | 4-F-phenyl | O |
| 2-pyrazinyl | pyrazol-1-yl | H | H | H | H | 4-Cl-phenyl | O |

TABLE 1-continued
| Het | R¹ | R² | R³ | R⁴ | R⁵ | R⁶ | X |
|---|---|---|---|---|---|---|---|
| 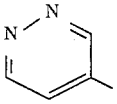 |  | H | H | H | H | 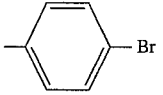 | O |
| 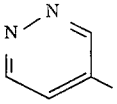 |  | H | H | H | H | 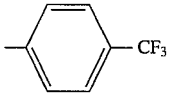 | O |
| 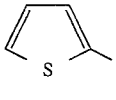 | 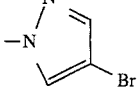 | H | H | H | H | 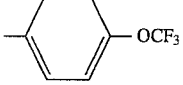 | O |
| 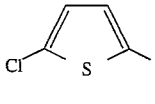 |  | H | H | H | H | 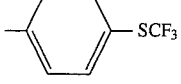 | O |
| 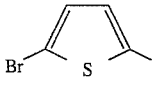 | 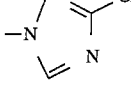 | H | H | H | H | 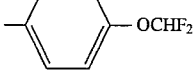 | O |
| 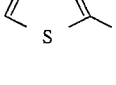 |  | H | H | H | H | 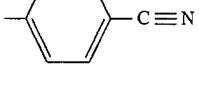 | O |
| 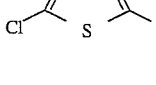 | 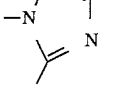 | H | H | H | H | 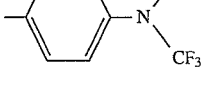 | O |
| 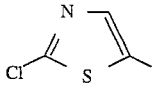 | 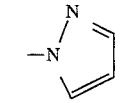 | H | H | H | H | 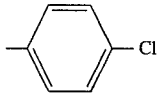 | O |
| 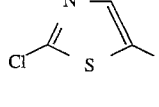 | 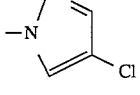 | H | H | H | H | 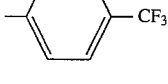 | O |
| 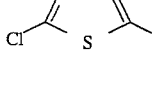 | 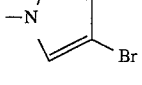 | H | H | H | H | 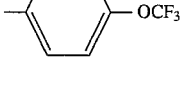 | O |
| 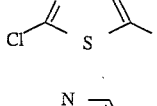 | 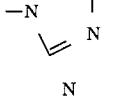 | H | H | H | H | 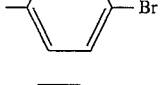 | O |
| 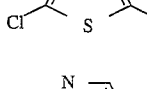 | 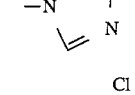 | H | H | H | H |  | O |
| 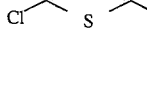 | 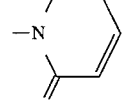 | H | H | H | H |  | |

TABLE 1-continued

| Het | R¹ | R² | R³ | R⁴ | R⁵ | R⁶ | X |
|---|---|---|---|---|---|---|---|
| 2,3-dichloro-5-methylpyridinyl | 4-chloropyrazol-1-yl | H | H | H | H | 4-(CF₃)phenyl | O |
| thien-2-yl | 2-oxopyridin-1-yl | H | H | H | H | 3-F-4-(CF₃)phenyl | O |
| 5-chlorothien-2-yl | 5-chloro-2-oxopyridin-1-yl | H | H | H | H | 4-(OCF₃)phenyl | O |
| 5-chlorothien-2-yl | 2-oxopyridin-1-yl | H | H | H | H | 3-Cl-4-(OCF₃)phenyl | O |
| pyridin-2-yl | 5-chloro-2-oxopyridin-1-yl | H | H | H | H | 4-Cl-phenyl | O |
| 5-bromopyridin-2-yl | 5-chloro-2-oxopyridin-1-yl | H | H | H | H | 4-Br-phenyl | O |
| pyridin-2-yl | 2-oxopyridin-1-yl | H | H | H | H | 3,4-(OCF₂O)phenyl | O |
| thien-2-yl | 2-oxopyrrolidin-1-yl | H | H | H | H | 4-(CF₃)phenyl | O |
| thien-2-yl | 2-oxopiperidin-1-yl | H | H | H | H | 3,4-(OCF₂O)phenyl | O |
| 5-chlorothien-2-yl | 2-oxopyrrolidin-1-yl | H | H | H | H | 4-(OCF₃)phenyl | O |

TABLE 1-continued

| Het | R¹ | R² | R³ | R⁴ | R⁵ | R⁶ | X |
|---|---|---|---|---|---|---|---|
| 5-bromo-2-thienyl | N-morpholinonyl (N-C(=O)-CH₂-O-CH₂) | H | H | H | H | 4-chlorophenyl | O |
| 5-bromo-2-thienyl | N-(2-oxopiperidinyl) | H | H | H | H | 4-bromophenyl | O |
| 5-chloro-2-thienyl | N-(2-oxopiperidinyl) | H | H | H | H | 3-chloro-4-(trifluoromethoxy)phenyl | O |
| 2-thienyl | N-(2-oxopyrrolidinyl) | H | H | H | H | 3-fluoro-4-(trifluoromethyl)phenyl | O |
| 5-chloro-2-thienyl | N-morpholinonyl | H | H | H | H | 4-(trifluoromethylthio)phenyl | O |
| 2-pyridyl | N-(2-oxopyrrolidinyl) | H | H | H | H | 4-(difluoromethoxy)phenyl | O |
| 2-pyridyl | N-(2-oxopiperidinyl) | H | H | H | H | 4-chlorophenyl | O |
| 5-chloro-2-pyridyl | N-(2-oxopyrrolidinyl) | H | H | H | H | 4-bromophenyl | O |
| 5-bromo-2-pyridyl | N-(2-oxopyrrolidinyl) | H | H | H | H | 4-(trifluoromethyl)phenyl | O |
| 5-methyl-2-pyridyl | N-(2-oxopiperidinyl) | H | H | H | H | 3-chloro-4-(trifluoromethoxy)phenyl | O |
| 2-pyridyl | N-morpholinonyl | H | H | H | H | 4-(trifluoromethoxy)phenyl | O |

TABLE 1-continued

| Het | R¹ | R² | R³ | R⁴ | R⁵ | R⁶ | X |
|---|---|---|---|---|---|---|---|
| 2,3-dichloro-5-methylpyridinyl | 2-oxopyrrolidin-1-yl | H | H | H | H | 4-chlorophenyl | O |
| thiazol-2-yl | 4-chloropyrazol-1-yl | H | H | H | H | 4-bromophenyl | O |
| thiazol-2-yl | 4-bromopyrazol-1-yl | H | H | H | H | 4-trifluoromethoxyphenyl | O |
| thiazol-2-yl | 3-chloro-1,2,4-triazol-1-yl | H | H | H | H | 3,4-(difluoromethylenedioxy)phenyl | O |
| thiazol-2-yl | 2-oxopyrrolidin-1-yl | H | H | H | H | 4-(trifluoromethylthio)phenyl | O |
| thiazol-2-yl | 2-oxopyridin-1-yl | H | H | H | H | 4-bromophenyl | O |
| oxazol-2-yl | 4-chloropyrazol-1-yl | H | H | H | H | 4-(methylthio)phenyl | O |
| oxazol-2-yl | 4-bromopyrazol-1-yl | H | H | H | H | 3-fluoro-4-trifluoromethylphenyl | O |
| thien-2-yl | 5-trifluoromethylimidazol-1-yl | H | H | H | H | 4-chlorophenyl | O |
| 5-chlorothien-2-yl | imidazol-1-yl | H | H | H | H | 4-bromophenyl | O |
| 5-chlorothien-2-yl | 5-trifluoromethylimidazol-1-yl | H | H | H | H | 3,4-(difluoromethylenedioxy)phenyl | O |
| 5-bromothien-2-yl | 4,5-dichloroimidazol-1-yl | H | H | H | H | 4-trifluoromethoxyphenyl | O |

TABLE 1-continued

| Het | R¹ | R² | R³ | R⁴ | R⁵ | R⁶ | X |
|---|---|---|---|---|---|---|---|
| 4-bromo-5-thienyl | 1-imidazolyl | H | H | H | H | 3-Cl-4-OCF₃-phenyl | O |
| 5-chloro-2-thienyl | 4,5-dichloro-1-imidazolyl | H | H | H | H | 4-SCF₃-phenyl | O |
| 2-thienyl | 1-imidazolyl | H | H | H | H | 3-F-4-CF₃-phenyl | O |
| 5-chloro-2-thienyl | 5-CF₃-1-imidazolyl | H | H | H | H | 4-CF₃-phenyl | O |
| 2-pyrazinyl | 3-chloro-2-pyrazinyl | H | H | H | H | 3,4-(OCF₂O)-phenyl | O |
| 2-pyrazinyl | 3-chloro-2-pyrazinyl | H | H | H | H | 4-Cl-phenyl | O |
| 2-pyrazinyl | 2-pyridyl | H | H | H | H | 4-OCF₂Cl-phenyl | O |
| 2-pyrazinyl | 4-pyridyl | H | H | H | H | 4-SCF₂Cl-phenyl | O |
| 3-pyridazinyl | 2-pyridyl | H | H | H | H | 3,4-(OCF₂CF₂O)-phenyl | O |
| 3-pyridazinyl | 6-chloro-2-pyridyl | H | H | H | H | 4-CF₃-phenyl | O |
| 5-pyrimidinyl | 2-pyridyl | H | H | H | H | 4-Br-phenyl | O |
| 2-thienyl | 6-chloro-2-pyridyl | H | H | H | H | 4-Cl-phenyl | O |

TABLE 1-continued

| Het | R¹ | R² | R³ | R⁴ | R⁵ | R⁶ | X |
|---|---|---|---|---|---|---|---|
| 5-Cl-thiophen-2-yl | pyrazin-2-yl | H | H | H | H | 4-CF₃-phenyl | O |
| 5-Cl-thiophen-2-yl | pyrimidin-5-yl | H | H | H | H | 4-Br-phenyl | O |
| 5-Br-thiophen-2-yl | pyrazin-2-yl | H | H | H | H | 4-OCHF₂-phenyl | O |
| 5-Cl-thiophen-2-yl | pyridazin-3-yl | H | H | H | H | 4-SCH₃-phenyl | O |
| thiophen-2-yl | 3-Cl-6-CH₃-pyrazin-2-yl | H | H | H | H | 4-Cl-phenyl | O |
| 5-Cl-thiophen-2-yl | pyrimidin-5-yl | H | H | H | CH₃ | 4-OCF₃-phenyl | O |
| pyridin-2-yl | 6-Cl-pyridin-2-yl | H | H | H | H | 4-CF₃-phenyl | O |
| 6-Cl-pyridin-2-yl | pyridin-2-yl | H | H | H | H | 4-OCF₃-phenyl | O |
| 6-Cl-pyridin-2-yl | pyridin-2-yl | H | H | H | H | 4-Cl-phenyl | O |
| 6-Cl-pyridin-2-yl | 6-Cl-pyridin-2-yl | H | H | CH₃ | H | 4-Cl-phenyl | O |
| 5-CH₃-pyridin-2-yl | pyridin-2-yl | H | H | H | H | 2,3-(OCF₂O)-phenyl | O |
| 5,6-diCl-pyridin-2-yl | pyridin-2-yl | H | H | H | H | 3-F-4-CF₃-phenyl | O |
| thiazol-2-yl | pyridazin-3-yl | H | H | H | H | 4-CN-phenyl | O |

TABLE 1-continued

| Het | R¹ | R² | R³ | R⁴ | R⁵ | R⁶ | X |
|---|---|---|---|---|---|---|---|
| thiazol-2-yl | pyrazin-2-yl (methyl) | H | H | H | H | 4-Cl-phenyl | O |
| thiazol-2-yl | pyridazin-3-yl (methyl) | H | H | H | H | 4-Br-phenyl | O |
| thiazol-2-yl | 1-methyl-2-oxo-pyrimidin-yl | H | H | H | H | 4-NO₂-phenyl | O |
| pyridin-2-yl | pyridazin-3-yl (methyl) | H | H | H | H | 4-CF₃-phenyl | O |
| pyridin-2-yl | 1-methyl-2-oxo-pyridin-yl | H | H | H | H | 4-Cl-phenyl | O |
| 6-chloropyridin-3-yl | pyridazin-3-yl (methyl) | H | H | H | H | 4-Br-phenyl | O |
| pyridin-2-yl | 1-methyl-2-oxo-pyrimidin-yl | H | H | H | H | 3,4-(OCF₂CF₂O)-phenyl | O |
| furan-2-yl | 4-chloro-pyrazol-1-yl | H | H | H | H | 4-Cl-phenyl | O |
| 5-methylfuran-2-yl | 4-bromo-pyrazol-1-yl | H | H | H | H | 4-Br-phenyl | O |
| 5-methylfuran-2-yl | pyridin-2-yl (methyl) | H | H | H | H | 4-CF₃-phenyl | O |
| 5-methylfuran-2-yl | 4-bromo-pyrazol-1-yl | H | H | H | H | 3-F-4-CF₃-phenyl | O |
| 5-methylthiophen-2-yl | pyrazol-1-yl | H | H | H | H | 3-Cl-4-OCF₃-phenyl | O |

TABLE 1-continued
| Het | R¹ | R² | R³ | R⁴ | R⁵ | R⁶ | X |
|---|---|---|---|---|---|---|---|
| 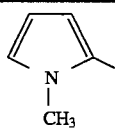 | 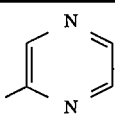 | H | H | H | H | 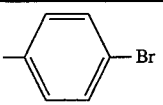 | O |
| 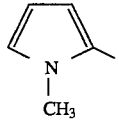 | 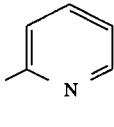 | H | H | H | H | 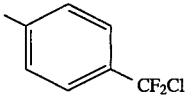 | O |
| 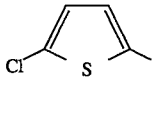 | 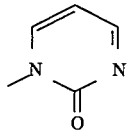 | H | H | H | H | 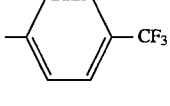 | O |
| 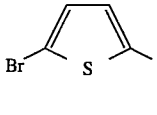 | 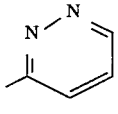 | H | H | H | H | 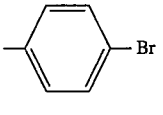 | O |
| 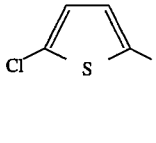 | 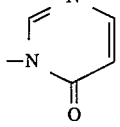 | H | H | H | H | 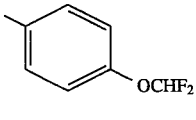 | O |
| 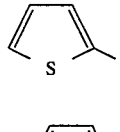 | 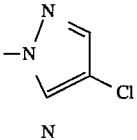 | H | H | H | H | 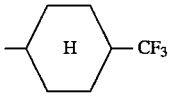 | O |
| 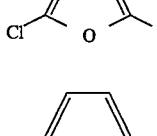 | 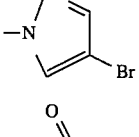 | H | H | H | H | 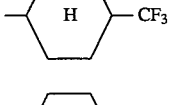 | O |
| 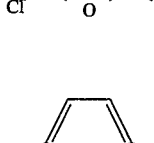 | 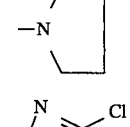 | H | H | H | H | 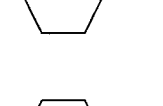 | O |
| 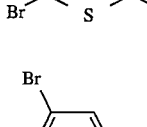 | 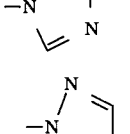 | H | H | H | H | 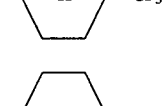 | O |
| 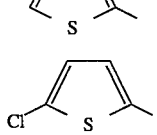 | 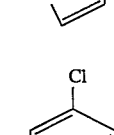 | H | H | H | H | 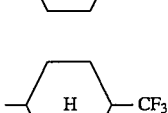 | O |
|  | 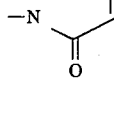 | H | H | H | H |  | O |

TABLE 1-continued

| Het | R¹ | R² | R³ | R⁴ | R⁵ | R⁶ | X |
|---|---|---|---|---|---|---|---|
| 2-thienyl | 1-methyl-2-oxo-pyridin-3-yl | H | H | H | H | 4-CF₃-cyclohexyl | O |
| 5-chloro-2-furyl | 1-methyl-2-oxo-piperidin-3-yl | H | H | H | H | 4-CF₃-cyclohexyl | O |
| 5-bromo-2-thienyl | 1-methyl-2-oxo-pyrrolidin-3-yl | H | H | H | H | 4-CF₃-cyclohexyl | O |
| pyridin-2-yl | 4-chloro-pyrazol-1-yl | H | H | H | H | 4-CF₃-cyclohexyl | O |
| pyridin-2-yl | 4-bromo-pyrazol-1-yl | H | H | H | H | 4-CF₃-cyclohexyl | O |
| 6-chloro-pyridin-3-yl | 4-iodo-pyrazol-1-yl | H | H | H | H | 4-CF₃-cyclohexyl | O |
| 6-bromo-pyridin-3-yl | pyrazol-1-yl | H | H | H | H | 4-CF₃-cyclohexyl | O |
| 5-methyl-pyridin-2-yl | 3-chloro-1,2,4-triazol-1-yl | H | H | H | H | 4-CF₃-cyclohexyl | O |
| pyridin-3-yl | 5-chloro-2-oxo-pyridin-1-yl | H | H | H | H | 4-CF₃-cyclohexyl | O |
| 5,6-dichloro-pyridin-2-yl | 1-methyl-2-oxo-pyridin-3-yl | H | H | H | H | 4-CF₃-cyclohexyl | O |
| 5-chloro-2-thienyl | pyrazin-2-yl | H | H | H | H | 4-CF₃-cyclohexyl | O |
| 5-chloro-2-thienyl | pyridazin-3-yl | H | H | H | H | 4-CF₃-cyclohexyl | O |

TABLE 1-continued

| Het | R¹ | R² | R³ | R⁴ | R⁵ | R⁶ | X |
|---|---|---|---|---|---|---|---|
| 5-bromo-thien-2-yl | N-methyl-pyrimidin-2(1H)-on-yl | H | H | H | H | 4-CF₃-cyclohexyl | O |
| pyrid-2-yl | pyrazin-2-yl | H | H | H | H | 4-CF₃-cyclohexyl | O |
| pyrid-2-yl | pyridazin-3-yl | H | H | H | H | 4-CF₃-cyclohexyl | O |
| 5-chloro-thien-2-yl | 1-(N-methylcarbamoyl)-2-(1-trifluoromethyl)ethylidene-hydrazino | H | H | H | H | 4-OCF₃-phenyl | O |
| pyrid-2-yl | 1-(N-methylcarbamoyl)-2-(phenyl)methylene-hydrazino | H | H | H | H | 4-Cl-phenyl | O |
| 5-chloro-pyrid-2-yl | 1-(N-methylcarbamoyl)-2-(4-chlorophenyl)methylene-hydrazino | H | H | H | H | 4-CF₃-phenyl | O |
| 5-bromo-thien-2-yl | 1-(N-methylcarbamoyl)-2-(1-methyl)ethylidene-hydrazino | H | H | H | H | 4-Br-phenyl | O |
| pyrid-2-yl | 1-(carbamoyloxy)-2-(1-trifluoromethyl)ethylidene-hydrazino | H | H | H | H | 4-SCF₃-phenyl | O |

If, for example, 3-pyrid-4'-yl-pyrid-2"-yl-4,5-dihydropyrazole and 4-trifluoromethoxy-phenyl isocyanate are used as starting substances, the course of the reaction in process (A) according to the invention can be represented by the following equation:

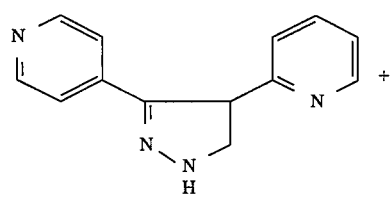

+

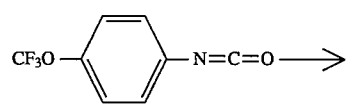

⟶

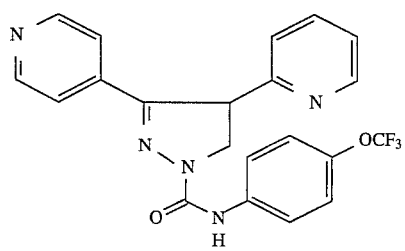

If, for example, 3-pyrid-4'-yl-4-pyrid-2"-yl-4,5-dihydropyrazole and N-(4-trifluoromethoxyphenyl)-carbamoyl chloride are used as starting substances, the course of the reaction in process (B) according to the invention can be represented by the following equation:

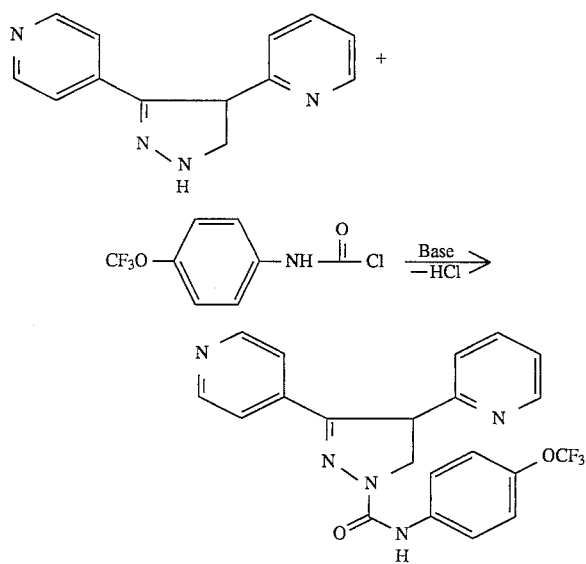

Formula (II) provides a general definition of the pyrazoline derivatives required as starting substances for carrying out processes (A) and (B) according to the invention. In this formula (II), $R^1$, $R^2$, $R^3$, $R^4$ and Het preferably represent those radicals which have already been mentioned as preferred for these substituents in connection with the description of the substances of the formula (I) according to the invention. The pyrazoline derivatives of the formula (II) are new and can be prepared by one of the following processes: they are prepared by reaction of compounds of the formula (VI)

with hydrazine hydrate in a polar organic solvent, preferably an alkanol, at temperatures of 20° to 80° C. in particular at 30° to 60° C.:

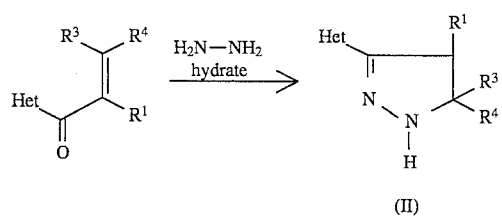

Depending on the meaning of the substituents $R^3$ and $R^4$, the following preparation variants result here for the starting compounds of the formula (VI)

(a) $R^3$ and $R^4$ in the formula (VI) represent hydrogen

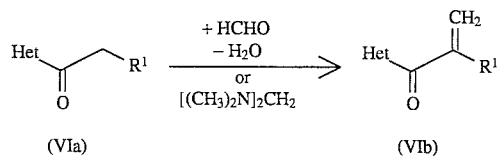

In this reaction, compounds of the formula (VIa) are either reacted with a formalin solution in a polar organic solvent, preferably an alkanol, and in particular in ethanol or methanol, with addition of small amounts of an organic base, in particular piperidine, and addition of glacial acetic acid, or reacted with bis-(dimethylamino)-methane in acetic anhydride.

(b) In the formula (VI), $R^3$ represents alkyl or aryl and $R^4$ represents hydrogen

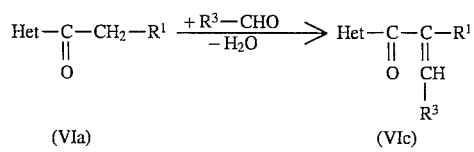

The process conditions correspond to those of the reaction with formaldehyde.

(c) In the formula (VI), $R^3$ and $R^4$ represent alkyl:

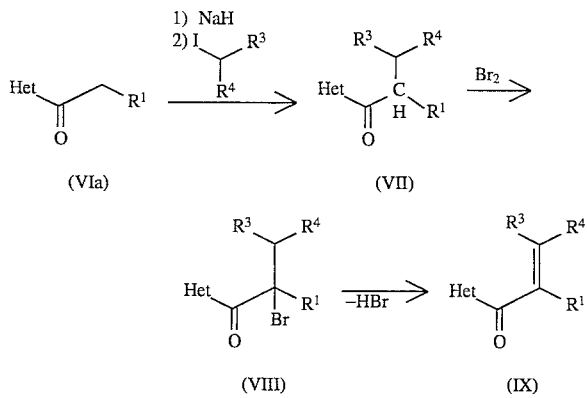

In this reaction, the compound (VI) is first converted into the salt with a strong base, and the salt is then reacted with a halide, in particular an iodide of the formula

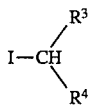

The compound of the formula (VII) formed in this reaction is brominated and the intermediate product of the formula (IX) is then prepared by addition of a base, HBr being eliminated.

Compounds of the formula (IIa) in which $R^3$ and $R^4$ represent hydrogen are also obtained by reaction of compounds of the formula (VId)

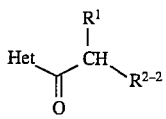

in which

Het and $R^1$ have the abovementioned meaning and $R^{2-2}$ represents hydrogen or alkyl, by first heating these in a 1st stage with one mole of N N-dimethylmethyleneimmonium chloride of the formula (XI)

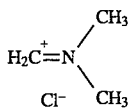

in a polar organic solvent, preferably acetonitrile, at temperatures of 10° to 100° C., in particular at 20° to 80° C., if appropriate under reflux, the intermediate product of the formula (XII)

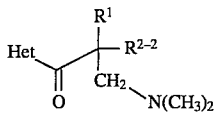

which intermediately occurs being isolated if appropriate, and then cyclising the intermediate product in a second stage with hydrazine hydrate in a polar organic solvent, preferably an alcohol, at temperatures of 20° to 80° C., in particular at 30° to 60° C., to give compounds of the formula (II).

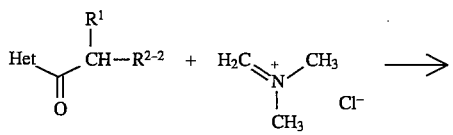

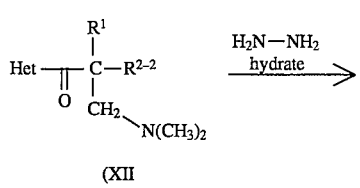

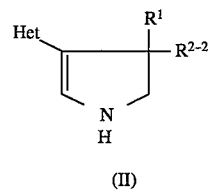

Compounds of the formula (XII) can also be prepared (a) by reaction by compounds of the formula (VId) with dimethylamine hydrochloride and paraformaldehyde in an alkanol at 30° to 80° C. and subsequent precipitation of the salt with a non-polar solvent, for example ether, or (b) by reaction of compounds of the formula (VId) with bis(dimethylamino)-methane in chloroform, toluene or acetonitrile at 30° to 80° C.:

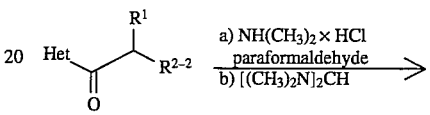

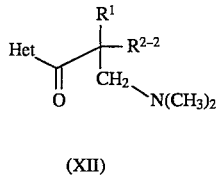

Some of the compounds of the formula (VIa) and (VIb) are new. They can be obtained by one of the processes described below:

(a) Compounds of the formula (VIa) and (VIb) in which $R^1$ represents a heterocyclic ring bonded via nitrogen are obtained by a process in which compounds of the formula (X)

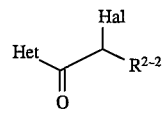

wherein $R^{2-2}$ represents hydrogen or alkysl,

Het has the abovementioned meaning and

Hal represents halogen, in particular bromine, are reacted with heterocyclic compounds of the formula (XIII)

$R^{1-1}$—H  (XIII)

wherein $R^{1-1}$ represents an optionally substituted pyrrolyl, pyrazolyl, imidazolyl, pyridonyl, pyrimidonyl, 1,2,3-triazolyl, 1,2,4-triazolyl or tetrazolyl radical, or represents an azolinone, azolinethione or azolinimine radical, which is unsubstituted or mono- or disubstituted by identical or different substituents and bonded via nitrogen, from the series comprising

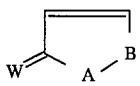

-continued

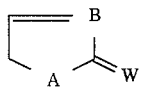 (R¹-c)

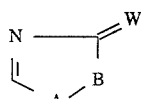 (R¹-e)

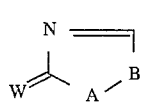 (R¹-f)

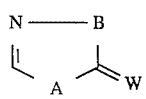 (R¹-h)

oder

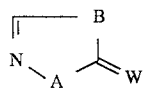 (R¹-i)

wherein
one of the groups A or B represents nitrogen and in each case the other (A or B) represents oxygen or sulphur, or represents the group -Nalkyl($C_1$-$C_4$—), or represents a methylene grouping —$CH_2$—, or represents a —CH— group and
W represents oxygen or sulphur, or represents a heterocyclic ring which is unsubstituted or mono- to trisubstituted, from the series comprising

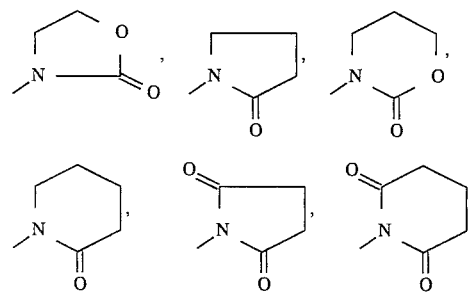

with the aid of an organic or inorganic base, hydrogen halide being eliminated.

(b) Compounds of the formula (VIa) and (VIb) in which $R^1$ represents a heterocyclic ring bonded via carbon are obtained (b-α) by a process in which compounds of the formula (XIV)

Het—$R^{12}$ (XIV)

$R^{12}$ represents a cyano or alkoxycarbonyl group, preferably cyano, methoxycarbonyl or ethoxycarbonyl, are reacted with heterocyclic compounds of the formula (XV)

$R^{1\text{-}2}$—$CH_3$ (XV)

in which
$R^{1\text{-}2}$ represents an optionally substituted pyridinyl, pyrimidinyl, pyrazinyl, pyridazinyl or triazinyl radical, either in the presence of alkyllithium compounds, such as, for example, n-butyl-lithium, in an inert organic solvent, such as, for example, tetrahydrofuran, at −50° C. to +10° C. in particular −30° C. to −15° C., if appropriate in the presence of an inert gas atmosphere, such as, for example, argon, or are reacted with metal hydrides, such as, for example, sodium hydride, in dimethylformamide, or with strong bases, such as, for example, potassium hydroxide, or (b-β) by a process in which heterocyclic compounds of the formula (XVI)

Het—H (XVI)

in which
Het has the abovementioned meaning, are reacted with compounds of the formula (XVII)

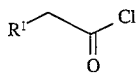 (XVII)

in which
$R^1$ has the abovementioned meaning, if appropriate in the presence of an inert organic solvent, such as, for example, hexane or chloroform, with Lewis acids, such as, for example, aluminium chloride, at temperatures between 30° C. and 130° C.

The compounds of the formulae (X), (XIII), (XIV), (XV), (XVI) and (XVII) are generally known compounds of organic chemistry.

The compounds of the formula (IV) required for carrying out process (B) according to the invention are likewise generally known compounds of organic chemistry.

The active compounds are suitable for combating animal pests, preferably arthropods and nematodes, in particular insects and arachnids, encountered in agriculture, in animal keeping, in forests, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa sppl. *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varive stis,* Atomaria spp., *Oryzaephilus surinamensis,* Antho nomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Cono derus spp., *Melolontha melolontha, Amphimallon solsti tialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Hydrotaea spp., Haematobia spp., Glossina spp., Melophagus spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*.

From the order of the Siphonaptera, for example, *Xenopsylla cheopis,* Ceratophyllus spp, and Ctenocephalides spp.

From the order of the Arachnida, for example, *Scorpio maurus* and *Latrodectus mactans*.

From the order of the Acarina, for example, *Acarus siro,* Argas spp., Ornithodoros spp., *Dermanyssus gallinae,* Ornithonyssus spp., *Eriophyes ribis, Phyllocoptruta oleivora,* Boophilus spp., Rhipicephalus spp., Amblyomma spp., Hyalomma spp., Ixodes spp., Dermacentor spp., Haemaphysalis spp., Otobius spp., Psoroptes spp., Chorioptes spp., Sarcoptes spp., Psorergates spp., Demodex spp., Notoedres spp., Tarsonemus spp., *Bryobia praetiosa,* Panonychus spp. and Tetranychus spp.

The active compounds according to the invention are not only active against plant, hygiene and stored product pests, but also, in the veterinary medicine sector, against animal parasites (ectoparasites and endoparasites), such as scaly ticks, argasidae, scab mites, trombidae, flies (stinging and sucking), parasitic fly larvae, lice, hair lice, bird lice, fleas and worms which live as parasites.

They are active against normally sensitive and resistant species and strains, as well as against all parasitic and non-parasitic stages of development of the ecto- and endoparasites.

The active compounds according to the invention are distinguished by a high insecticidal and acaricidal activity.

They can be employed particularly successfully for combating insects which are harmful to plants, such as, for example, against the larvae of the mustard beetle (*Phaedon cochleariae*) or against the tobacco bud caterpillar (*Heliothis virescens*) or against the caterpillars of the cabbage moth (*Plutella maculipennis*).

In addition, they can also be employed particularly successfully for combating parasitic pests of warm-blooded animals, such as, for example, the larvae of the gold fly (*Lucilia cuprina*) or against *Musca domestica* and against *Periplaneta americana*.

The active compounds can be converted to the customary formulations, such as solutions, emulsions, suspensions, powders, foams, pastes, granules, aerosols, natural and synthetic substances impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example, ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example, non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example, lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, attractants, sterilising agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms prepared from these formulations, as a mixture with synergistic agents. Synergistic agents are compounds which increase the action of the active compounds, without it being necessary for the synergistic agent added to be actively effective itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating insects, mites, ticks etc. in the sectors of animal keeping and cattle breeding; better results, for example higher milk production, greater weight, more attractive animal pelt, longer life etc., can be achieved by combating the pests.

The application of the active compounds according to the invention occurs in this sector in a known fashion, such as by external application in the form of, for example, dipping, spraying, pouring-on, spotting-on and dusting, as well as by means of parenteral application in the form, for example, of injection, and, furthermore, by means of the feed-through method. In addition, application as shaped articles (collar, ear tag) is also possible, as is application in the form of so-called treatment of the surroundings.

The following examples describe the preparation and the use of active compounds according to the invention, without limiting them thereto.

PREPARATION EXAMPLES

EXAMPLE 1

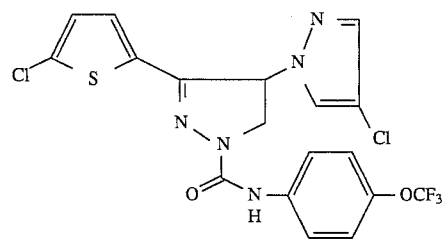

3.9g (0.0174 mol) of 3-pyrid-4'-yl-4-pyrid-2"-yl-4,5-dihydropyrazole are dissolved in 20 ml of anhydrous acetonitrile at 50° C., 3.25 g (0.016 mol) of 4-trifluoromethoxyphenyl isocyanate are added, and 2 drops of triethylamine are added. The mixture is allowed to stand at 20° C. for 2 hours and is then concentrated in vacuo. 20 ml of diethyl ether are added to the residue, and after 2 hours the crystalline precipitate is filtered off with suction.

1.1 g of 3-pyrid-4'-yl-4-pyrid-2"-yl-4,5-dihydro-pyrazole-1-carboxylic acid 4'"-trifluoromethoxyanilide are obtained as colourless crystals of melting point 172° C.

The end products of the formula (I) listed below in Table 2 are obtained analogously to Example 1 and in accordance with the general preparation instructions:

TABLE 2

![Structure I: Het-C(R1)=... pyrazoline with N-N, R2, R3, R4, R5, R6, X substituents]

(I)

| Ex. No. | Het | R¹ | R² | R³ | R⁴ | R⁵ | R⁶ | X | Physical constants [M.p.: °C.] |
|---|---|---|---|---|---|---|---|---|---|
| 2 | 4-pyridyl | 2-pyridyl | H | H | H | H | 4-Cl-phenyl | O | 159 |
| 3 | 4-pyridyl | 2-pyridyl | H | H | H | H | 4-CF₃-phenyl | O | 206 |
| 4 | 4-pyridyl | 2-pyridyl | H | H | H | H | 2-Cl-4-SCClF₂-phenyl | O | 208 |
| 5 | 5-Br-thien-2-yl | 4-Cl-1-methylpyrazol-3-yl | H | H | H | H | 4-Cl-phenyl | O | 193 |
| 6 | 5-Cl-thien-2-yl | 4-Cl-1-methylpyrazol-3-yl | H | H | H | H | 4-CF₃-phenyl | O | 171 |
| 7 | 5-Cl-thien-2-yl | 4-Cl-1-methylpyrazol-3-yl | H | H | H | H | 4-OCF₃-phenyl | O | 179 |
| 8 | 5-Cl-thien-2-yl | 4-Cl-1-methylpyrazol-3-yl | H | H | H | H | 4-Br-phenyl | O | 195 |
| 9 | 5-Cl-thien-2-yl | 4-Cl-1-methylpyrazol-3-yl | H | H | H | H | 4-Cl-phenyl | O | >230 |

TABLE 2-continued

| Ex. No. | Het | R¹ | R² | R³ | R⁴ | R⁵ | R⁶ | X | Physical constants [M.p.: °C.] |
|---|---|---|---|---|---|---|---|---|---|
| 10 | Br–S– | Cl-pyrazolyl | H | H | H | H | –C₆H₄–CF₃ | O | 177 |
| 11 | Br–S– | Cl-pyrazolyl | H | H | H | H | –C₆H₄–OCF₃ | O | 186 |
| 12 | Br–S– | Cl-pyrazolyl | H | H | H | H | –C₆H₄–Br | O | 187 |

Preparation of the precursors:

Example (II-1)

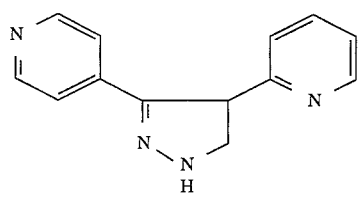

23.8 g (0.12 mol) of α-pyrid-2-yl-4-acetyl-pyridine are dissolved in 80 ml of acetonitrile at 20° to 30° C., 15 g (0.15 mol) of N,N-dimethylmethyleneimmonium chloride are added and the mixture is heated at 80° C. for 1½ hours. Thin layer chromatography is used to check that the reaction is complete. The mixture is cooled to 50° C. and 20 ml of hydrazine hydrate are then added. The mixture is subsequently stirred at 20°–40° C. for a further 30 minutes and then concentrated to about one third in vacuo, 100 ml of water are added and the mixture is extracted with 150 ml of diethyl ether. The ether phase is separated off, dried (MgSO₄) and concentrated in vacuo.

18.3 g of 3-pyrid-4'-yl-4-pyrid-2"-yl-4,5-dihydropyrazole are obtained as a brown oil which is used further without additional purification.

[¹H-NMR* (CDCl₃); δ=4.70–4.755 (IH,m), 4.06–4.16 (IH,m); 3.77–3.82 (IH,m)].

*H-NMR spectra were recorded in deuterated chloroform (CDCl₃) using tetramethylsilane (TMS) as the internal standard. The chemical shift δ in ppm is stated.

The precursors of the formula (II) listed below in Table 3 are obtained analogously to Example (II-1) and in accordance with the general preparation instructions:

TABLE 3

| Ex. No. | Het | R¹ | R² | R³ | R⁴ | Physical constants [M.p.: °C.] |
|---|---|---|---|---|---|---|
| II-2 | Br–S– | Cl-pyrazolyl | H | H | H | 139 |

Preparation of the starting substances:

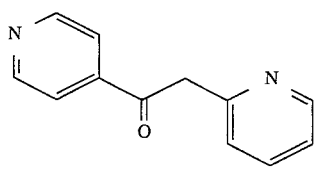

8.6 g (0.2 mol) of α-picoline are dissolved in 200 ml of anhydrous tetrahydrofuran at room temperature under an inert gas atmosphere (argon). 80 ml of a solution of n-butyllithium in hexane (content: 2.5 mol/l ) are then added dropwise at −70° C. The reaction mixture is subsequently stirred at 0° C. for 1 hour, and 20.8 g (0.2 mol) of 4-cyanopyridine dissolved in 50 ml of anhydrous tetrahydrofuran are then added dropwise, likewise at 0° C. During this addition, the temperature rise to 30° C., and the mixture is then subsequently stirred at 20° C. for a further 30 minutes. 100 ml of water are then added to the reaction mixture, the mixture is subsequently extracted with 200 ml of diethyl ether, the organic phase is separated off and dried (MgSO$_4$), and the solvent is stripped off in vacuo. The residue is then stirred with a mixture of petroleum ether/diethyl ether 1:1 and the crystals formed are filtered off with suction.

28.76 g (72.5% of theory) of 2-(4-methyl-2-pyrydinyl)-1-(4-pyridinyl)ethanone are obtained as yellow crystals of melting point 112° C.

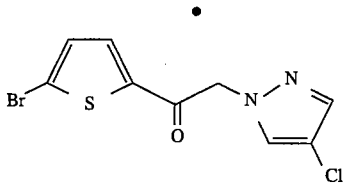

11.63 g (0.118 mol) of 4-chloropyrazole hydrochloride are suspended in 100 ml of absolute acetonitrile, and 34.5 g (0.25 mol) of powdered potassium carbonate are added. 32.37 g (0.118 mol) of 2-bromo-5-(2-bromoacetyl)thiophene dissolved in 50 ml of absolute acetonitrile are then added dropwise and the reaction mixture is heated under reflux for 1 hour. It is stirred into 300 ml of water and extracted with methylene chloride. The extract is dried over sodium sulphate, the solvent is evaporated off in vacuo and the residue is recrystallised from ethyl acetate.

4.9 g (about 16% of theory) of 2-(4-chloro- 1-pyrazolyl )-1-(2-bromo-5-thienyl )-ethanone of melting point 127° C. are obtained.

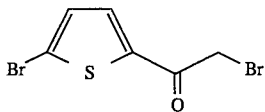

19.36 g (0,121 mol) of bromine are added dropwise to a solution of 24.8 g (0.121 mol) of 2-acetyl-5-bromothiophene in 120 ml of methylene chloride at 0° to 5° C. and the batch is stirred at this temperature for 1 hour. After warming to room temperature, the reaction mixture is stirred into 200 ml of ice-water and extracted with methylene chloride. The organic phase is washed twice with ice-water and dried over sodium sulphate and the solvent is stripped off in vacuo.

32.4 g (94% of theory) of 2-bromo-5-(2-bromoacetyl)thiophene of melting point 79° C. are obtained.

Use examples

The compounds shown below were employed as comparison substances in the following use examples:

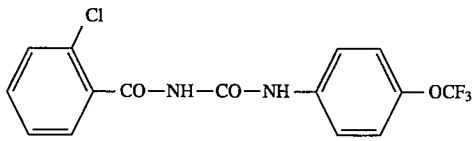

Triflumuron=2-chloro-N[[[4-(trifluoromethoxy)-phenyl]amino]-carbonyl]-benzamide (known from: DE-A 2601780)

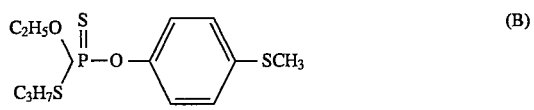

Sulprofos=O-(ethyl-O-(4-methylthio)-phenyl)-S-propyl dithiophosphate (known from: DE-A 2111414)

Example A

Phaedon larvae test

Solvent: 7 parts by weight of dimethylformamide
Emulsifier: 1 part by weight of alkylaryl polyglycol ether To prepare a suitable preparation of active compound 1 part-by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the desired time, the destruction in % is determined. 100% means that all the beetle larvae have been killed; 0% means that none of the beetle larvae have been killed.

In this test, for example, the following compounds of the preparation examples show a superior activity compared with the prior art: 6, 9, 10, 11 and 12.

Example B

Plutella test

Solvent: 7 parts by weight of dimethylformamide
Emulsifier: 1 part by weight of alkylaryl polyglycol ether To prepare a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the cabbage moth (*Plutella maculipennis*) while the leaves are still moist.

After the desired time, the destruction in % is determined. 100% means that all the caterpillars have been killed; 0% means that none of the caterpillars have been killed.

In this test, for example, the following compounds of the preparation examples show a superior activity compared with the prior art: 7.

Example C

Heliothis virescens test

Solvent: 7 parts by weight of dimethylformamide
Emulsifier: 1 part by weight of alkylaryl polyglycol ether To prepare a suitable preparation of active compound, 1 part by weight of active compound is mixed with the stated amount of solvent and the stated amount of emulsifier, and the concentrate is diluted with water to the desired concentration.

Soya shoots (*Glycine max*) are treated by immersion in the preparation of active compound at the desired concentration, and infested with the tobacco bud caterpillar (*Heliothis virescens*) while the leaves are still damp.

After the desired time the destruction in % is determined. 100% here means that all the caterpillars were killed; 0% means that no caterpillars were killed.

In this test, the following compounds from the Preparation Examples, for instance, display superior activity with respect to the prior art: 5, 6, 7, 8, 9, 10, 11 and 12.

Example D

Blowfly larvae test

Test organisms: Larvae of *Lucilia cuprina*

Emulsifier: 35 parts by weight of ethylene glycol monomethyl ether 35 parts by weight of nonylphenol polyglycol ether To produce a suitable preparation of active compound, three parts by weight of active compound are mixed with seven parts by weight of the abovementioned mixture and the emulsion concentrate thus obtained is diluted with water to the particular desired concentration.

About 20 larvae of *Lucilia cuprina* res. are introduced into a test tube which contains approx. 1 cm³ of horse meat and 0.5 ml of the preparation of active compound. After 24 hours, the efficiency of the active compound preparation is determined. 100% here means that all of the blowfly larvae have been killed; 0% means that none of the blowfly larvae have been killed.

In this test, the compounds from Preparation Examples 6, 7, 8 and 11, for example, displayed an outstanding activity.

Example E

Moth test

Test animals: *Blattella germanca* or *Periphaneta americana*

Solvent: 35 parts by weight of ethylene glycol monomethyl ether 35 parts by weight of nonylphenol polyglycol ether To produce a suitable formulation, three parts by weight of active compound are mixed with seven parts by weight of the solvent/emulsifier mixture stated above, and the emulsion concentrate thus obtained is diluted with water to the particular desired concentration.

2 ml of this active compound preparation are pipetted onto filter paper discs (ø 9.5 cm) in Petri dishes of corresponding size. After drying the filter discs, 5 test animals in the case of *B. germanica* or of *P. americana*, respectively, were transferred and covered.

After 3 days, the efficiency of the active compound preparation is determined. The efficiency is expressed in % 100% means that all the moths have been killed; 0% means that no moths have been killed.

In this test, compound 6 from the Preparation Examples, for instance, displays an outstanding activity at 1000 ppm.

Example F

Fly test

Test organisms: *Musca domestica*, strain WHO(N)

Solvent: 35 parts by weight of ethylene glycol monomethyl ether 35 parts by weight of nonylphenol polyglycol ether To produce a suitable formulation, three parts by weight of active compound are mixed with seven parts of the above-stated solvent/emulsifier mixture, and the emulsion concentrate thus obtained is diluted with waters to the particular desired concentration.

2 ml of this active compound preparation are pipetted onto filter paper discs (ø 9.5 cm) which are in Petri dishes of appropriate size. After drying the filter discs, 25 test organisms are transferred to the Petri dishes and covered.

After 6 hours, the efficiency of the active compound preparation is determined. The efficiency is expressed in % .In this scale, 100% means that all the flies have been killed; 0% means that none of the flies have been killed.

In this test, compound 7 from the Preparation Examples, for instance, displays outstanding activity at 1000 ppm.

We claim:

1. A substituted 3,4-hetaryl-pyrazoline of the formula

in which $R^1$ represents an optionally substituted pyrrolyl, pyrazolyl, imidazolyl, 1,2,3-triazolyl, tetrazolyl, pyridonyl, 1,2,4-triazolyl or triazinyl radical, or $R^1$ furthermore represents an azolinone, azolinethione or azolinimino radical, which is unsubstituted or mono- or disubstituted by identical or different substituents and bonded via nitrogen, selected from the group consisting of

 ($R^1$-a)

 ($R^1$-b)

 ($R^1$-c)

 ($R^1$-d)

 ($R^1$-e)

 ($R^1$-f)

 ($R^1$-g)

 ($R^1$-h)

51

-continued

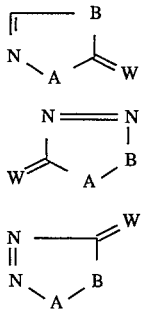

(R¹-i)

(R¹-k)

(R¹-l)

and

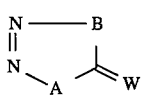

(R¹-m)

wherein
one of the groups A or B represents nitrogen and in each case the other (A or B) represents oxygen or sulphur, or represents the group —N-alkyl($C_1$-$C_4$—), or represents a methylene grouping —$CH_2$— or a CH group, W represents oxygen or sulphur, or represents the group —N-alkyl ($C_1$-$C_4$), or $R^1$ furthermore represents a heterocyclic ring, which is unsubstituted or mono- to trisubstituted, selected from the group consisting of

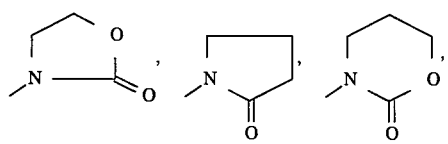

and

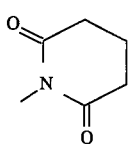

wherein said substituents on the heterocyclic rings identified above are selected from the group consisting of fluorine, chlorine, bromine, iodine, cyano, nitro, hydroxyl, amino, alkyl($C_1$-$C_4$), alkoxy($C_1$-$C_4$), alkyl($C_1$-$C_4$)thio, halogenoalkyl($C_1$-$C_2$), halogenoalkoxy($C_1$-$C_2$), halogenoalkyl($C_1$-$C_2$)thio, alkyl($C_1$-$C_3$)amino, dialkyl($C_1$-$C_3$)amino, dihalogenoalkyl ($C_1$-$C_2$)amino, alkoxy($C_1$-$C_4$)carbonyl and phenyl which is optionally substituted by fluorine, chlorine, bromine, methyl, ethyl, methoxy, ethoxy, halogenoalkyl($C_1$-$C_2$), halogenoalkoxy($C_1$-$C_2$) or halogenoalkyl($C_1$-$C_2$)thio, $R^2$ represents hydrogen, alkyl($C_1$-$C_4$), cycloalkyl($C_3$-$C_6$) which is optionally substituted by fluorine, chlorine, bromine or halogenoalkyl($C_1$-$C_3$); halogenoalkyl($C_1$-$C_3$)thio or alkoxy($C_1$-$C_4$)carbonyl, $R^3$ represents hydrogen or alkyl($C_1$-$C_4$),

52

$R^4$ represents hydrogen or alkyl($C_1$-$C_4$), $R^5$ represents hydrogen, alkyl($C_1$-$C_4$), phenyl or alkyl($C_1$-$C_3$)thio, $R^6$ represents alkyl($C_1$-$C_4$) which is optionally substituted by fluorine, chlorine, bromine, halogenoalkyl($C_1$-$C_3$) or halogenoalkoxy($C_1$-$C_3$), or represents cycloalkyl($C_3$-$C_6$) which is optionally substituted by fluorine, chlorine, bromine, halogenoalkyl($C_1$-$C_3$) or halogenoalkoxy($C_1$-$C_3$), or represents the radical

wherein
$R^{10}$ and $R^{11}$ can be identical or different and represent hydrogen, fluorine, chlorine, bromine, iodine, alkyl($C_1$-$C_4$), nitro, cyano, halogenoalkyl($C_1$-$C_3$), alkoxy($C_1$-$C_4$), halogenoalkoxy($C_1$-$C_3$), alkyl($C_1$-$C_3$)thio, halogenoalkyl($C_1$-$C_3$)thio, phenoxy which is optionally substituted by fluorine, chlorine, bromine, halogenoalkyl($C_1$-$C_3$), alkoxy($C_1$-$C_3$) or alkyl($C_1$$C_3$), mono- or dialkylamino having in each case 1 to 4 carbon atoms in the alkyl radical and optionally substituted by fluorine, chlorine, bromine, alkoxy($C_1$$C_3$) or halogenoalkyl($C_1$-$C_3$), or cyanoalkyl($C_3$-$C_6$) which is optionally substituted by alkyl($C_1$-$C_3$), alkoxy($C_1$-$C_3$), fluorine, chlorine, bromine or alkyl($C_1$-$C_3$)thio, or wherein $R^{10}$ and $R^{11}$ together represent a divalent radical selected from the group consisting of

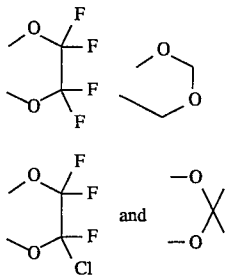

X represents oxygen or sulphur and

Het represents a thienyl radical which is unsubstituted or mono- to trisubstituted by identical or different substituents selected from the group consisting of methyl, ethyl, n-propyl, i-propyl, tert-butyl, fluorine, chlorine, bromine, iodine, halogenoalkyl($C_1$-$C_3$), methoxy, ethoxy, n-propyloxy, i-propyloxy, alkyl($C_1$-$C_3$)thio, halogenoalkoxy($C_1$-$C_3$), halogenoalkyl($C_1$-$C_3$)thio, alkoxy($C_1$-$C_3$)carbonyl, phenoxy or phenylthio which is optionally substituted by fluorine, chlorine, bromine, methyl, ethyl, methoxy, ethoxy or halogenoalkyl($C_1$-$C_3$), alkenyl($C_3$-$C_4$)oxy, alkinyl($C_2$-$C_4$), alkyl($C_1$-$C_3$)thionyl, alkyl($C_1$-$C_3$)sulphonyl, halogenoalkyl($C_1$$C_3$)thionyl, halogenoalkyl ($C_1$-$C_3$)sulphonyl, nitro and cyano, or wherein two adjacent positions are bonded to one another by a 3,4-methylenedioxy or 3,4-ethylenedioxy radical which is substituted by fluorine and/or chlorine.

2. A substituted 3,4-hetaryl-pyrazoline according to claim 1, in which

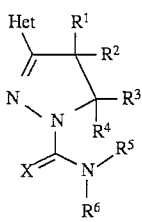 (I)

in which

R¹ represents an optionally substituted pyrrolyl, pyrazolyl, imidazolyl, 1,2,3-triazolyl, tetrazolyl, pyridonyl, 1,2,4-triazolyl or triazinyl radical, or R¹ furthermore represents an azolinone, azolinethione or azolinimino radical, which is unsubstituted or mono- or disubstituted by identical or different substituents and bonded via nitrogen, selected from the group consisting of

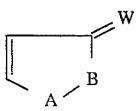 (R¹-a)

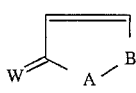 (R¹-b)

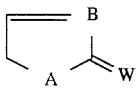 (R¹-c)

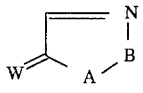 (R¹-d)

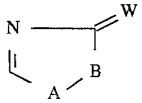 (R¹-e)

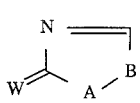 (R¹-f)

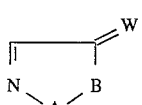 (R¹-g)

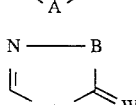 (R¹-h)

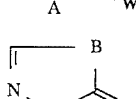 (R¹-i)

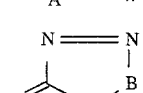 (R¹-k)

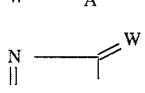 (R¹-l)

and

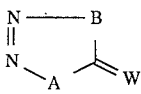 (R¹-m)

wherein one of the groups A or B represents nitrogen and in each case the other (A or B) represents oxygen or sulphur, or represents the group —N-alkyl($C_1$–$C_4$—), or represents a methylene grouping —$CH_2$— or a CH group, W represents oxygen or sulphur, or represents the group —N-alkyl ($C_1$–$C_4$), or R¹ furthermore represents a heterocyclic ring, which is unsubstituted or mono- to trisubstituted, selected from the group consisting of

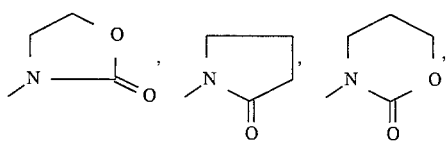

and

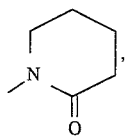, wherein said substituents on the heterocyclic rings identified above are selected from the group consisting of fluorine, chlorine, bromine, iodine, cyano, nitro, hydroxyl, amino, alkyl($C_1C_2$), alkoxy($C_1$–$C_4$), alkyl($C_1$–$C_4$)thio, halogenoalkyl($C_1$–$C_2$), halogenoalkoxy($C_1$–$C_4$), halogenoalkyl($C_1$–$C_2$)thio, alkyl($C_1$–$C_3$)amino, dialkyl($C_1$–$C_3$)amino, dihalogenoalkyl ($C_1$–$C_2$)amino, alkoxy($C_1$–$C_4$)carbonyl and phenyl which is optionally substituted by fluorine, chlorine, bromine, methyl, ethyl, methoxy, ethoxy, halogenoalkyl($C_1C_2$), halogenoalkoxy($C_1$–$C_2$) or halogenoalkyl($C_1$–$C_2$)thio, R² represents hydrogen, alkyl($C_1$–$C_4$), cycloalkyl($C_3$–$C_6$) which is optionally substituted by fluorine, chlorine, bromine or halogenoalkyl($C_1$–$C_3$); halogenoalkyl($C_1$–$C_3$)thio or alkoxy($C_1$–$C_4$)carbonyl, R³ represents hydrogen or alkyl($C_1$–$C_4$), R⁴ represents hydrogen or alkyl($C_1$–$C_4$), R⁵ represents hydrogen, alkyl($C_1$–$C_4$), phenyl or alkyl($C_1$–$C_3$)thio, R⁶ represents alkyl($C_1$–$C_4$) which is optionally substituted by fluorine, chlorine, bromine, halogenoalkyl($C_1$–$C_3$) or halogenoalkoxy($C_1$–$C_3$), or represents cycloalkyl($C_3$–$C_6$) which is optionally substituted by fluorine, chlorine, bromine, halogenoalkyl($C_1C_3$) or halogenoalkoxy($C_1$–$C_3$), or represents the radical

wherein

R¹⁰ and R¹¹ can be identical or different and represent hydrogen, fluorine, chlorine bromine, iodine, alkyl($C_1$–$C_4$), nitro, cyano, halogenoalkyl($C_1$–$C_3$), alkoxy($C_1$–$C_4$), halogenoalkoxy($C_1$–$C_3$), alkyl($C_1C_3$)thio, halogenoalkyl($C_1C_3$)thio, phenoxy which is optionally substituted by fluorine, chlorine, bromine, halogenoalkyl($C_1$–$C_3$), alkoxy($C_1$–$C_3$) or alkyl($C_1$–$C_3$), mono- or dialkylamino having in each case 1 to 4 carbon atoms in the alkyl radical and optionally substituted by fluorine, chlorine, bromine, alkoxy($C_1$–$C_3$) or halogenoalkyl($C_1$–$C_3$), or cycloalkyl($C_3$–$C_6$) which is optionally substituted by alkyl($C_1$–$C_3$), alkoxy($C_1$–$C_3$), fluorine, chlorine, bromine or alkyl($C_1$–$C_3$)thio, or wherein $R^{10}$ and $R^{11}$ together represent a divalent radical selected from the group consisting of

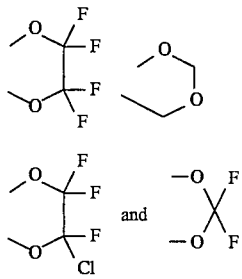

X represents oxygen or sulphur and

Het represents a thienyl radical which is unsubstituted or mono to trisubstituted by identical or different substituents selected from the group consisting of methyl, ethyl, n-propyl, i-propyl, tert-butyl, fluorine, chlorine, bromine, iodine, halogenoalkyl($C_1$–$C_3$), methoxy, ethoxy, n-propyloxy, i-propyloxy, alkyl($C_1$–$C_3$)thio, halogenoalkoxy($C_1$–$C_3$), halogenoalkyl($C_1$–$C_3$)thio, alkoxy($C_1$–$C_3$)carbonyl, phenoxy or phenylthio which is optionally substituted by fluorine, chlorine, bromine, methyl, ethyl, methoxy, ethoxy or halogenoalkyl($C_1$–$C_3$), alkenyl($C_3$–$C_4$)oxy, alkinyl($C_2$–$C_3$), alkyl($C_1$–$C_3$)thionyl, alkyl($C_1$–$C_3$)sulphonyl, halogenoalkyl($C_1$–$C_3$)thionyl, halogenoalkyl($C_1$–$C_3$)sulphonyl, nitro and cyano, or wherein two adjacent positions are bonded to one another by a 3,4-methylenedioxy or 3,4-ethylenedioxy radical which is substituted by fluorine and/or chlorine.

3. A compound according to claim 1, wherein such compound is 3(5-chloro-thien-2'-yl)-4-(4''-chloro-pyrazole)- 1-carboxylic acid 4'''-trifluoromethoxyanilide of the formula

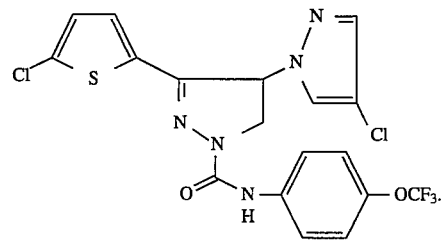

4. An ectoparasiticidal, endoparasiticidal, arthropodicidal or nematocidal composition comprising an amount effective therefor of a compound according to claim 1 and a diluent.

5. A method of combatting ectoparasites, endoparasites, arthropods or nematodes which comprises applying thereto or to their habitat an amount effective therefor of a compound according to claim 1 and a diluent.

6. The method according to claim 5, wherein such compound is 3-(5-chloro-thien-2'-yl)-4-(4''-chloro-pyrazole)- 1-carboxylic acid 4'''-trifluoromethoxyanilide.

* * * * *

UNITED STATES PATENT AND TRADEMARK OFFICE
CERTIFICATE OF CORRECTION

PATENT NO. : 5,502,070
DATED : March 26, 1996
INVENTOR(S) : Fuchs, et al.

It is certified that error appears in the above-indentified patent and that said Letters Patent is hereby corrected as shown below:

Col. 54, line 33    Delete " alkyl($C_1C_2$) " and substitute -- alkyl($C_1$-$C_4$) --

Col. 54, line 35    Delete " halogenoalkoxy($C_1$-$C_4$) " and substitute -- halogenoalkoxy($C_1$-$C_2$) --

Col. 54, line 56    After " halogenoalkyl($C_1$ " insert -- - --

Col. 55, line 2     After " alkyl($C_1$ " insert -- - --, after " halogenoalkyl($C_1$" insert -- - --

Col. 56, line 3     Delete " alkinyl($C_2$-$C_3$) " and substitute -- alkinyl($C_2$-$C_4$) --

Signed and Sealed this

Twentieth Day of August, 1996

Attest:

BRUCE LEHMAN

*Attesting Officer*     *Commissioner of Patents and Trademarks*